United States Patent [19]

Mitchell

[11] Patent Number: 5,086,543
[45] Date of Patent: Feb. 11, 1992

[54] WRAPPING DEVICE

[76] Inventor: Jacob T. Mitchell, 3615 147th Pl. NE #C1, Bellevue, Wash. 98007

[21] Appl. No.: 512,303

[22] Filed: Sep. 10, 1990

[51] Int. Cl.$^5$ .................................................. B65D 63/00
[52] U.S. Cl. .................................... 24/16 PB; 24/16 R
[58] Field of Search .................. 24/16 R, 16 PB, 306, 24/442; 248/205.2; 128/DIG. 15; 2/DIG. 6

[56] References Cited

U.S. PATENT DOCUMENTS

| | | | |
|---|---|---|---|
| 3,000,384 | 9/1961 | Piers, Jr. | 128/DIG. 15 |
| 3,086,529 | 4/1963 | Munz et al. | 128/DIG. 15 |
| 3,372,438 | 3/1968 | Rinecker | 24/16 R |
| 3,376,865 | 4/1968 | Gamper | 128/DIG. 15 |
| 3,947,927 | 4/1976 | Rosenthal | 24/16 R |
| 4,417,710 | 11/1983 | Adair | 248/205.2 |
| 4,684,559 | 8/1987 | Wasko | 2/DIG. 6 |
| 4,700,432 | 10/1987 | Fennell | 24/16 R |
| 4,712,766 | 12/1987 | Ehrenhalt | 24/16 R |

Primary Examiner—Victor N. Sakran
Attorney, Agent, or Firm—Hughes & Multer

[57] ABSTRACT

A wrapping device in the form of an elastic strip of material varying in length and width, yet sufficient for wrapping around objects. Fastener portions which are pressure sensitive and adapted for releasable engagement are attached at the ends of the opposite sides of the material and sometimes near the center which enables the device to be adjustably secured around objects of varying sizes. The fastener portions are such that forces applied by the objects tending to separate them place interacting parts of the fastener portion in shear or tension, rather than peel. A release loop is attached to the exposed end of the strip of material to aid in disengagement of the fastener portions. A loop tab may be attached near the center of the exposed side of the strip of material to allow the wrapping device to be placed in a hanging position.

4 Claims, 2 Drawing Sheets

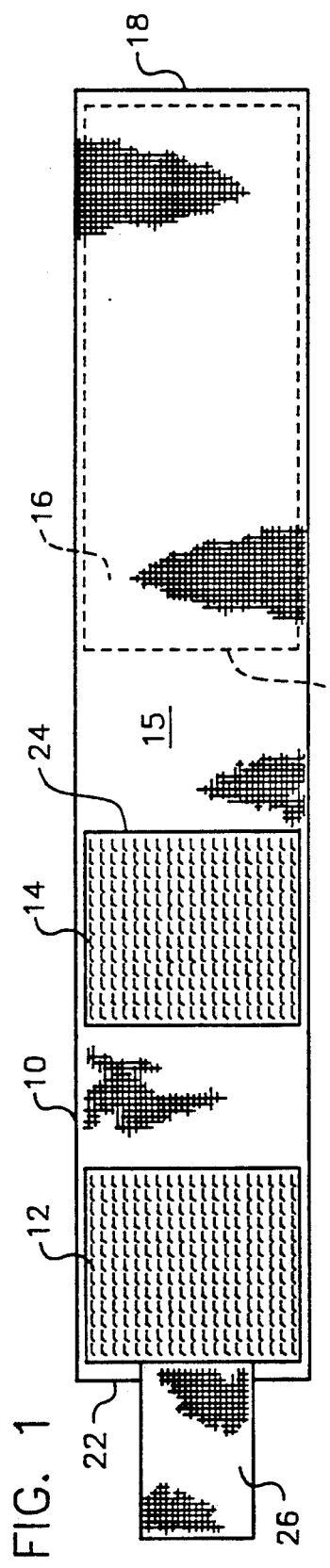
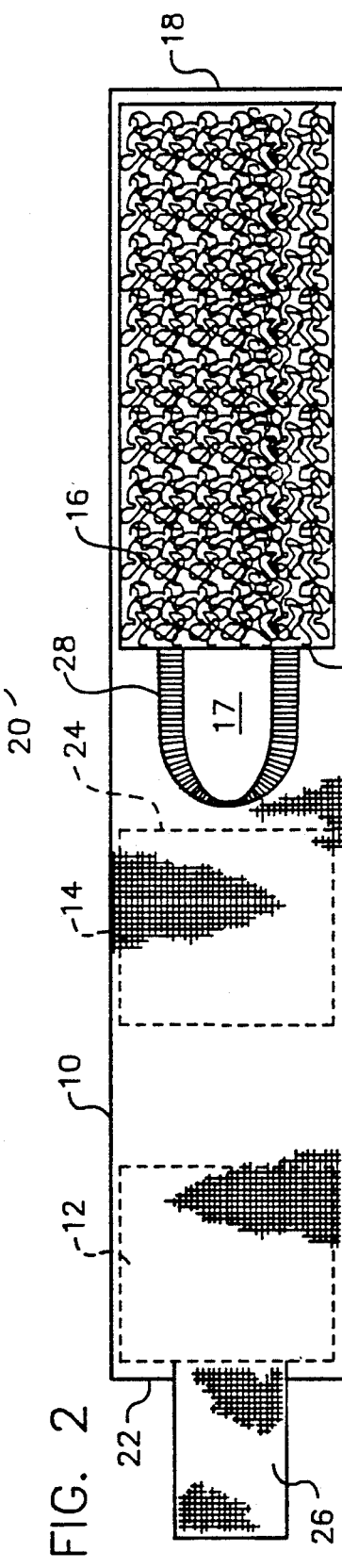
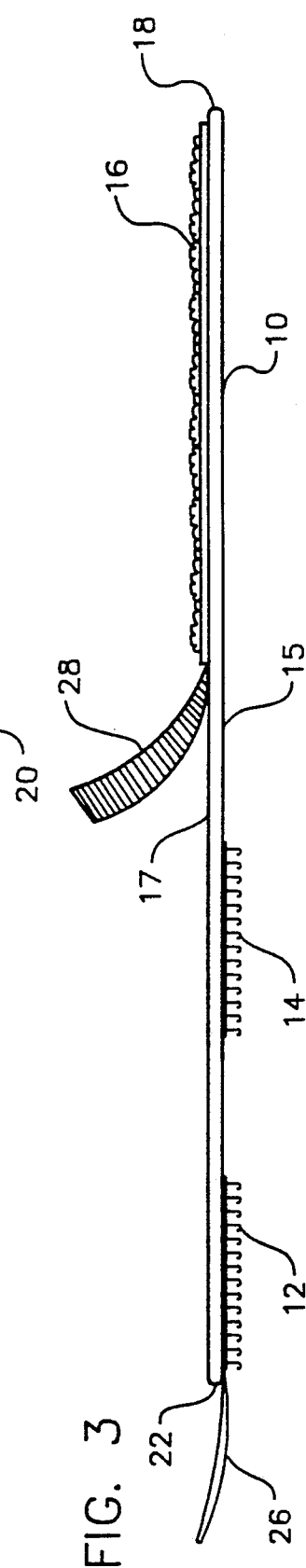
FIG. 1
FIG. 2
FIG. 3

WRAPPING DEVICE

BACKGROUND OF THE INVENTION

1. Field of the Invention

The present invention relates to a wrapping device, and more particularly to a wrapping device including an elastic strip adapted to encircle and to permit the simultaneous carrying of two spaced, independent articles and to permit rapid release of the articles from the wrapping device.

2. Related Art

The following previously-issued patents are of interest in connection with the present invention:
U.S. Pat. No. 4,700,432, Fennell, issued Apr. 25, 1986;
U.S. Pat. No. 3,372,438, Wayne, issued Nov. 23, 1966; and
U.S. Pat. No. 3,947,927, Rosenthal, issued Aug. 26, 1974.

SUMMARY OF THE INVENTION

Briefly stated, in accordance with one aspect of the present invention, a wrapping device is provided for encircling a pair of spaced, independent articles and for securely gripping the articles to permit them to be carried together in spaced relationship. The device includes a continuous, unitary, elongated elastic band having a length sufficient to encircle a pair of separate and distinct articles when the articles are positioned in closely spaced relationship. The band has an upper face and a lower face and also has a first end and a second end.

A first elongated area of hook and loop fastening material is secured to the upper face of the band and extends along the band from the first end to a first termination point substantially intermediate the ends of the band. Second and third areas of hook and loop fastening material are provided and are each adapted to securely and releasably engage with the first area of hook and loop fastening material. The second and third areas of fastening material are secured to the lower face of the band, the second area of fastening material positioned adjacent the second end of the band and defining a first connection surface, the third area of fastening material positioned adjacent the second area and spaced therefrom to permit longitudinal extension of the band between the second and third areas of fastening material. The third area of fastening material terminates at a second termination point spaced from the first termination point.

The band is adapted to pass completely around a first article with the lower face of the band in contact with the first article, and with the first and third fastening material areas engaged so that the band securely grips the first article. The space between the second and third fastening material areas overlies a part of a second article spaced from the first article by at least the thickness of the band and of the first fastening material. The first and second fastening material areas are engaged so that the band securely and releasably grips the second article.

BRIEF DESCRIPTION OF THE DRAWINGS

FIG. 1 is a bottom view of a wrapping device in accordance with the present invention.

FIG. 2 is a top view of the wrapping device shown in FIG. 1.

FIG. 3 is a cross-sectional view of the wrapping device shown in FIG. 1.

DESCRIPTION OF THE PREFERRED EMBODIMENTS

Figure 4:
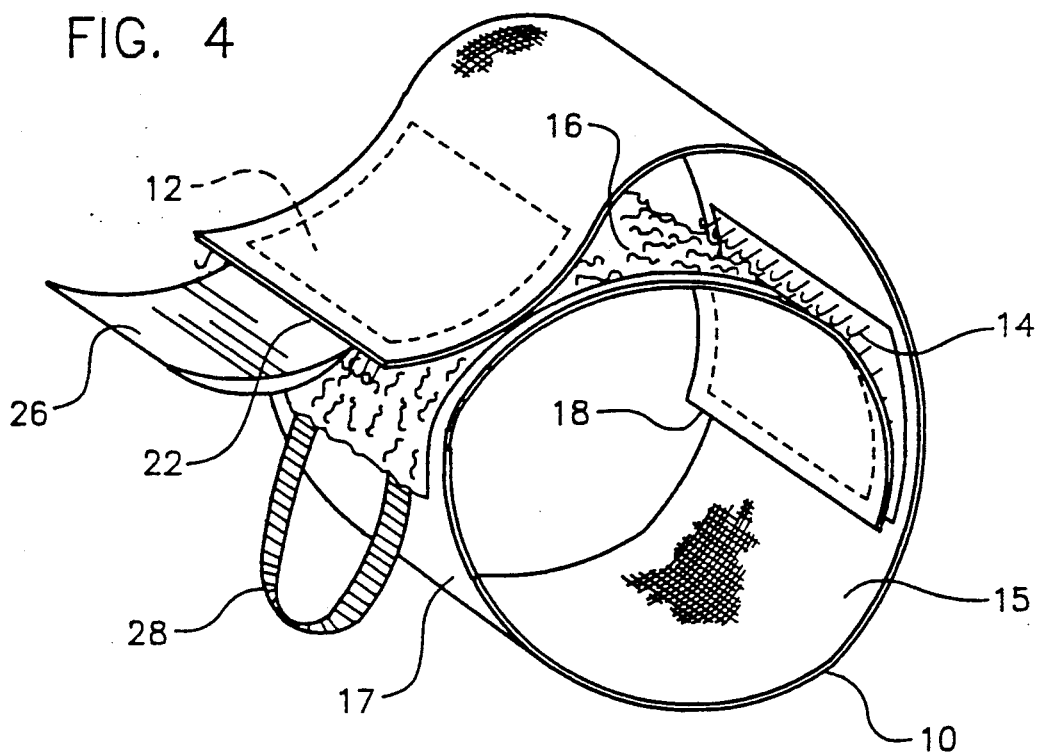
FIG. 4 is a ¾ view of the wrapping device of FIG. 1 when the device is in use.
Figure 5:
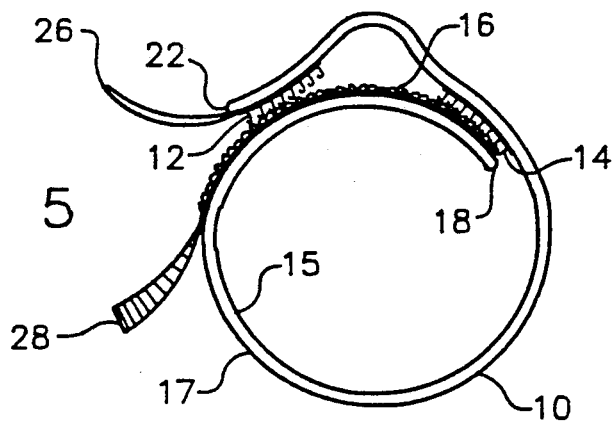
FIG. 5 is a cross-sectional view of the wrapping device shown in FIG. 4.

Referring to the drawings, and particularly to FIGS. 1 and 2 thereof, there is shown a band 10, which preferably is made from a woven elastic material. The length and width of band 10 are dependent upon the application for which it is intended to be used, but are sufficient for wrapping around objects.

Band 10 includes Velcro fastener portions in the form of hook portions 12 and 14 on one side 15 of band 10, and loop portion 16 on the opposite side 17 of band 10. Loop portion 16, which is longer than each of hook portions 12 and 14, extends inwardly along band 10 from end 18 thereof to a first termination point 20 that is substantially intermediate the ends 18 and 22 of band 10.

Hook portion 12 is adjacent end 22 of band 10 and defines a first connection surface connectable with loop portion 16. Hook portion 14 is positioned inwardly of hook portion 12 along side 15 of band 10 and is spaced therefrom a distance sufficient to permit extension of band 10 between hook portion 12 and hook portion 14. The inner termination point 24 of hook portion 14 is spaced from first termination point 20 to permit extension of band 10 between termination points 20 and 24.

When in assembled form around a pair of articles, the band in accordance with the present invention is as shown in FIGS. 3 and 4. Band 10 is adapted to pass completely around a first article (not shown) with the face 15 of band 10 in contact with the first article and with loop portion 16 engaged with hook portion 14 to securely grip the article. The space defined between hook portions 12 and 14 overlies part of a second article (not shown) that is spaced from the first article by the thickness of band 10 and of loop portion 16. Hook portion 12 is in engagement with loop portion 16 so that the band securely and releasably grips the second article.

A release loop 26 extends from end 22 of band 10 to facilitate removal of the fastened band from about an article. Additionally, a loop tab 28 is secured to band 10 at first termination point 20 to permit hanging of the wrapping device from a hook (not shown).

Although particular embodiments of the present invention have been illustrated and described, it will be apparent to those skilled in the art that various changes and modifications can be made without departing from the spirit of the present invention. It is therefore intended to encompass within the appended claims all such changes and modifications that fall within the scope of the present invention.

I claim:

1. A wrapping device for encircling a pair of spaced, independent articles and for securely gripping the articles to permit them to be carried together in spaced relationship, said wrapping device comprising:

a. a continuous, unitary, elongated elastic band having a length sufficient to encircle a pair of separate and distinct articles when the articles are positioned in closely spaced relationship, the band having an upper face and a lower face and having a first end and a second end;

b. a first elongated area of hook and loop fastening material secured to the upper face of the band and extending along the band from the first end to a first termination point substantially intermediate the ends of the band;

c. second and third area of hook and loop fastening material each adapted to securely and releasably engage with the first area of hook and loop fastening material, the second and third area of fastening material secured to the lower face of the band, the second area of fastening material positioned adjacent the second end of the band and defining a first connection surface, the third area of fastening material positioned adjacent the second area and spaced therefrom to permit longitudinal extension of the band between the second and third area of fastening material, the elasticity of the band between the second and third area permitting adjustment capability for accommodating articles of different size, the third area of fastening material terminating at a second termination point spaced from the first termination point;

d. the band is adapted to pass completely around a first article with the lower face of the band in contact with the first article and with the first and third fastening material areas engaged so that the band securely grips the first article, the space between the second and third fastening material area overlying a part of a second article spaced from the first article by at least the thickness of the band and of the first fastening material, the first and second fastening material area engage so that the band securely and releasably grips the second article.

2. A wrapping device in accordance with claim 1 wherein the first and third fastening material area are in spaced, non-overlapped relationship on the band so that the first and second termination points are spaced from each other to permit free elastic extension of the band therebetween for providing adjustment capability for accommodating articles of different size.

3. A wrapping device in accordance with claim 2 including a release loop extending from the second end of the band to facilitate removal of the fastened band from about an article.

4. A wrapping device in accordance with claim 3 including a loop tab positioned at the first termination point to permit hanging the wrapping device from a hook.

* * * * *